US 7,881,804 B2

(12) United States Patent
Bulkes et al.

(10) Patent No.: US 7,881,804 B2
(45) Date of Patent: Feb. 1, 2011

(54) COMPOSITE WAVEFORM BASED METHOD AND APPARATUS FOR ANIMAL TISSUE STIMULATION

(75) Inventors: Cherik Bulkes, Sussex, WI (US); Stephen Denker, Mequon, WI (US)

(73) Assignee: Kenergy, Inc., Mequon, WI (US)

( * ) Notice: Subject to any disclaimer, the term of this patent is extended or adjusted under 35 U.S.C. 154(b) by 993 days.

(21) Appl. No.: 11/685,903

(22) Filed: Mar. 14, 2007

(65) Prior Publication Data
US 2007/0219599 A1    Sep. 20, 2007

Related U.S. Application Data

(60) Provisional application No. 60/782,451, filed on Mar. 15, 2006.

(51) Int. Cl.
A61N 1/00       (2006.01)
(52) U.S. Cl. ........................................ 607/72
(58) Field of Classification Search ............ 607/72, 607/70, 45, 156, 2, 32, 5, 66, 9, 40, 129; 600/508, 529
See application file for complete search history.

(56) References Cited

U.S. PATENT DOCUMENTS

| | | | |
|---|---|---|---|
| 4,373,531 A | 2/1983 | Wittkampf et al. | |
| 4,494,545 A * | 1/1985 | Slocum et al. | 607/32 |
| 4,543,956 A | 10/1985 | Herscovici | |
| 4,972,846 A * | 11/1990 | Owens et al. | 607/129 |
| 5,279,292 A | 1/1994 | Baumann et al. | |
| 5,425,748 A * | 6/1995 | Pless | 607/5 |
| 5,531,779 A | 7/1996 | Dahl et al. | |
| 5,713,939 A | 2/1998 | Nedungadi et al. | |
| 5,739,795 A | 4/1998 | Chanteau et al. | |
| 5,741,316 A | 4/1998 | Chen et al. | |
| 5,814,089 A | 9/1998 | Stokes et al. | |
| 5,995,874 A | 11/1999 | Borza | |
| 6,026,818 A | 2/2000 | Blair et al. | |
| 6,029,090 A | 2/2000 | Herbst | |
| 6,067,474 A | 5/2000 | Schulman et al. | |
| 6,138,681 A | 10/2000 | Chen et al. | |
| 6,148,233 A * | 11/2000 | Owen et al. | 607/5 |
| 6,241,751 B1 | 6/2001 | Morgan et al. | |
| 6,266,567 B1 | 7/2001 | Ishikawa et al. | |
| 6,343,232 B1 * | 1/2002 | Mower | 607/9 |
| 6,431,175 B1 | 8/2002 | Penner et al. | |
| 6,438,427 B1 | 8/2002 | Rexhausen et al. | |
| 6,442,413 B1 | 8/2002 | Silver | |

(Continued)

FOREIGN PATENT DOCUMENTS

WO    WO 00/41766    7/2000

*Primary Examiner*—George Manuel
*Assistant Examiner*—Robert N Wieland
(74) *Attorney, Agent, or Firm*—Quarles & Brady LLP; George E. Haas

(57) ABSTRACT

A medical apparatus, for artificially stimulating internal tissue of an animal, applies a composite voltage pulse to a pair of electrodes implanted in the animal. The composite voltage pulse is formed by a first segment and a second segment contiguous with the first segment, both of which have generally rectangular shapes. The amplitude of the first segment is significantly greater than, e.g. at least three times, the amplitude of the second segment. However, the second segment has a significantly longer duration than the first segment, e.g. at least three times longer. Preferably the integrals of the first and second segments are substantially equal.

24 Claims, 3 Drawing Sheets

U.S. PATENT DOCUMENTS

| | | |
|---|---|---|
| 6,445,953 B1 | 9/2002 | Bulkes et al. |
| 6,678,562 B1 * | 1/2004 | Tepper et al. .................. 607/51 |
| 6,882,881 B1 | 4/2005 | Lesser et al. |
| 6,915,165 B2 * | 7/2005 | Forsell ........................ 607/40 |
| 6,917,833 B2 | 7/2005 | Denker et al. |
| 7,003,350 B2 | 2/2006 | Denker et al. |
| 7,033,322 B2 | 4/2006 | Silver |
| 2002/0005719 A1 | 1/2002 | Gilboa et al. |
| 2004/0015205 A1 | 1/2004 | Whitehurst et al. |
| 2005/0107847 A1 | 5/2005 | Gruber et al. |
| 2005/0187584 A1 | 8/2005 | Denker et al. |
| 2005/0203600 A1 | 9/2005 | Wallace et al. |
| 2005/0203602 A1 | 9/2005 | Wallace et al. |
| 2005/0222632 A1 | 10/2005 | Obino |
| 2006/0095078 A1 | 5/2006 | Tronnes |

* cited by examiner

COMPOSITE WAVEFORM BASED METHOD AND APPARATUS FOR ANIMAL TISSUE STIMULATION

CROSS-REFERENCE TO RELATED APPLICATIONS

This application claims benefit of U.S. Provisional Patent Application No. 60/782,451 filed Mar. 15, 2006.

STATEMENT REGARDING FEDERALLY SPONSORED RESEARCH OR DEVELOPMENT

Not Applicable

BACKGROUND OF THE INVENTION

1. Field of the Invention

The present invention relates to implantable stimulators, which deliver electrical stimulation pulses to tissue of an animal for therapeutic purposes, and more particularly to the waveforms of such electrical stimulation pulses.

2. Description of the Related Art

A remedy for people with slowed or disrupted natural heart activity is to implant a cardiac pacing device which is a small electronic apparatus that electrically stimulates the heart to beat at regular rates.

Typically a battery powered pacing device is implanted in the patient's chest and has sensor electrodes that detect natural electrical impulses associated with in the heart contractions. These sensed impulses are analyzed to determine when abnormal cardiac activity occurs, in which event a pulse generator is triggered to produce artificial electrical pulses. Wires carry these pulses to stimulation electrodes placed adjacent specific cardiac muscles, which when electrically stimulated contract the heart chambers. It is important that the electrodes be properly located to produce contraction of the heart chambers.

Modern cardiac pacing devices vary the stimulation to adapt the heart rate to the patient's level of activity, thereby mimicking the heart's natural action. The pulse generator modifies that rate by tracking electrical signals at the sinus node of the heart or by responding to other sensor signals that indicate body motion or respiration rate.

The waveforms of the stimulation pulses are integral to the pacing process and are a function of the characteristics of a pacing signal generator; the electrical leads connecting that generator to the pacing site; the contact interface between the lead and the pacing site; and physiological and electrical characteristics of the tissue to be stimulated. FIG. 1 illustrates a traditional rectangular conventional pacing pulse CP that is characterized by a nominal amplitude $V_{SO}$ that is "on" for a duration $T_{PO}$ of about 0.4 ms to 2.0 ms. The integral of the waveform pulse is denoted by area "A0" under the pulse.

In this context, the overall system impedance, including that of the tissues, is complex with both reactive and resistive components. Since the generator load impedance is reactive, a square waveform in the time-domain at the signal generator degenerates to a composite of exponential rise and decay curves at the pacing site. These waveforms are filtered by the tissue impedance wherein higher frequency components get attenuated at the pacing site. Therefore, for short timed waveforms, the effective pacing amplitude at the pacing site becomes reduced.

In order to stimulate tissues, the initial rate of change of voltage (dV/dt) (voltage slope) has an impact on pacing effectiveness. A faster rising waveform will stimulate sooner than a slowly rising waveform, even when the final pacing waveform amplitudes are the same at the signal generator. In the present context, due to the time constants involved, the waveform measured at the pacing site lags the waveform at the generator. As a consequence, fast rise and fall times at the signal generator appear significantly attenuated with slower slopes at the stimulation site. When the waveforms are very short in duration, the effect of the lagging results in the amplitude at the pacing site never reaching a final steady state amplitude, as the waveform returns to zero before the maximum amplitude is reached.

Designers of prior art systems, kept the overall stimulation current reduced by increasing the resistance of the electrical leads, which limited the peak current from the pacing generator. However, this approach also reduced the efficiency of the pacing system.

Prior tissue stimulation devices occasionally had a side effect of stimulating nerves in the vicinity of the primary site which resulted in muscle twitching that was very uncomfortable to the patient.

From the prior examples, there is a need for a stimulation method that has improved pacing efficiency in a manner that does not causes collateral nerve stimulation.

SUMMARY OF THE INVENTION

A medical apparatus is provided to artificially stimulate internal tissue of an animal. That apparatus comprises a first electrode and a second electrode connected to a stimulator for implantation into the animal. The stimulator responds to a control signal by applying a composite voltage pulse to the first and second electrodes. The composite voltage pulse has a first segment and a second segment contiguous with the first segment. The shapes of the first and second segments are defined for effective tissue stimulation.

The first segment has an amplitude that is at least three times greater than an amplitude of the second segment. The second segment preferably has a duration that is at least three times a duration of the first segment with the entire duration of the composite voltage pulse preferably being less than 0.5 milliseconds. In a preferred embodiment, an integral of the first segment is substantially equal to an integral of the second segment. There are two principal variations of the composite voltage pulse, in the first of which both the first segment and the second segment are positive with respect to a reference voltage level and in the second variation first segment is positive and the second segment is negative with respect to a reference voltage level.

In accordance with another aspect of the invention, a first conductor connects the first electrode to the stimulator and a second conductor connects the second electrode to the stimulator. The first and second conductors have a combined a resistance that is less than 100 ohms, and preferably less than 10 ohms. The stimulator applies a composite voltage pulse to the electrodes, wherein that pulse has a fast rising leading edge, e.g. 4 volts per 10 microseconds. The lower resistance and the fast rise time reduce the lag between waveform at the generator and at the stimulation site, wherein the initial rise of the waveform is generated by a higher peak voltage at the generator than that required for generating the conventional pacing waveform.

In a further aspect of the current invention, for each period of the waveform, the fast rising part of the leading segment of the waveform makes the trailing segment of the waveform more effective in tissue stimulation and the overall area under the curve (voltage amplitude vs. time) is less than the conventional pacing waveform with a consequent decrease in the overall power consumption.

DETAILED DESCRIPTION OF THE INVENTION

Although the present invention is being described in the context of a transvascular stimulation platform, it has equal applicability to conventional implanted stimulation devices.

Figure 2:
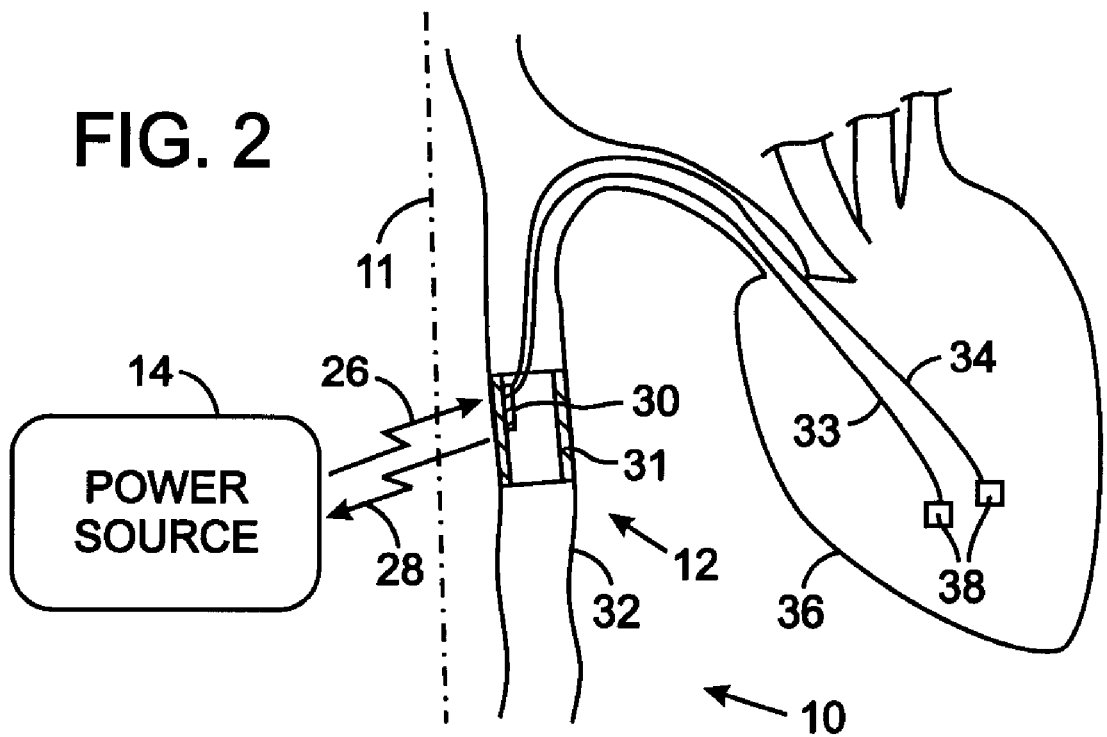
FIG. 2 is depicts a wireless transvascular platform for stimulating tissue inside a patient, wherein the platform includes external and internal components.

With initial reference to FIG. 2, a wireless transvascular platform 10 for tissue stimulation includes an extracorporeal power source 14 and a stimulator 12 implanted inside the body 11 of an animal. The extracorporeal power source 14 includes a battery that powers a transmitter that sends a first radio frequency (RF) signal 26 to the stimulator 12. The stimulator 12 derives electrical power from the energy of the first radio frequency signal 26 uses that power to energize and electronic circuit 30 mounted on an electronic carrier 31. The first radio frequency signal 26 also carries commands to configure the operation of the stimulator.

A second RF signal 28 enables the stimulator 12 to transmit operational data back to the extracorporeal power source 14. Such data may include physiological conditions of the animal, status of the stimulator and trending logs, for example, that have been collected by the implanted electronic circuit 30 and sent via the second radio frequency signal 28. This data mat be further transmitted by the extracorporeal power source 14 to remote monitoring equipment so that medical personnel can review the data or be alerted when a particular condition exists.

The implanted stimulator 12 includes the electronic circuit 30 mentioned above which has an RF transceiver and a tissue stimulation circuit, similar to that used in conventional pacemakers and defibrillators. That electronic circuit 30 is located in a large blood vessel 32, such as the inferior vena cava (IVC), for example. One or more, electrically insulated electrical conductors 33 and 34 extend from the electronic circuit 30 through the animal's blood vasculature to locations in the heart 36 where pacing and sensing are desired. The electrical conductors 33 and 34 terminate at stimulation electrodes 37 and 38 at those locations.

Figure 3:
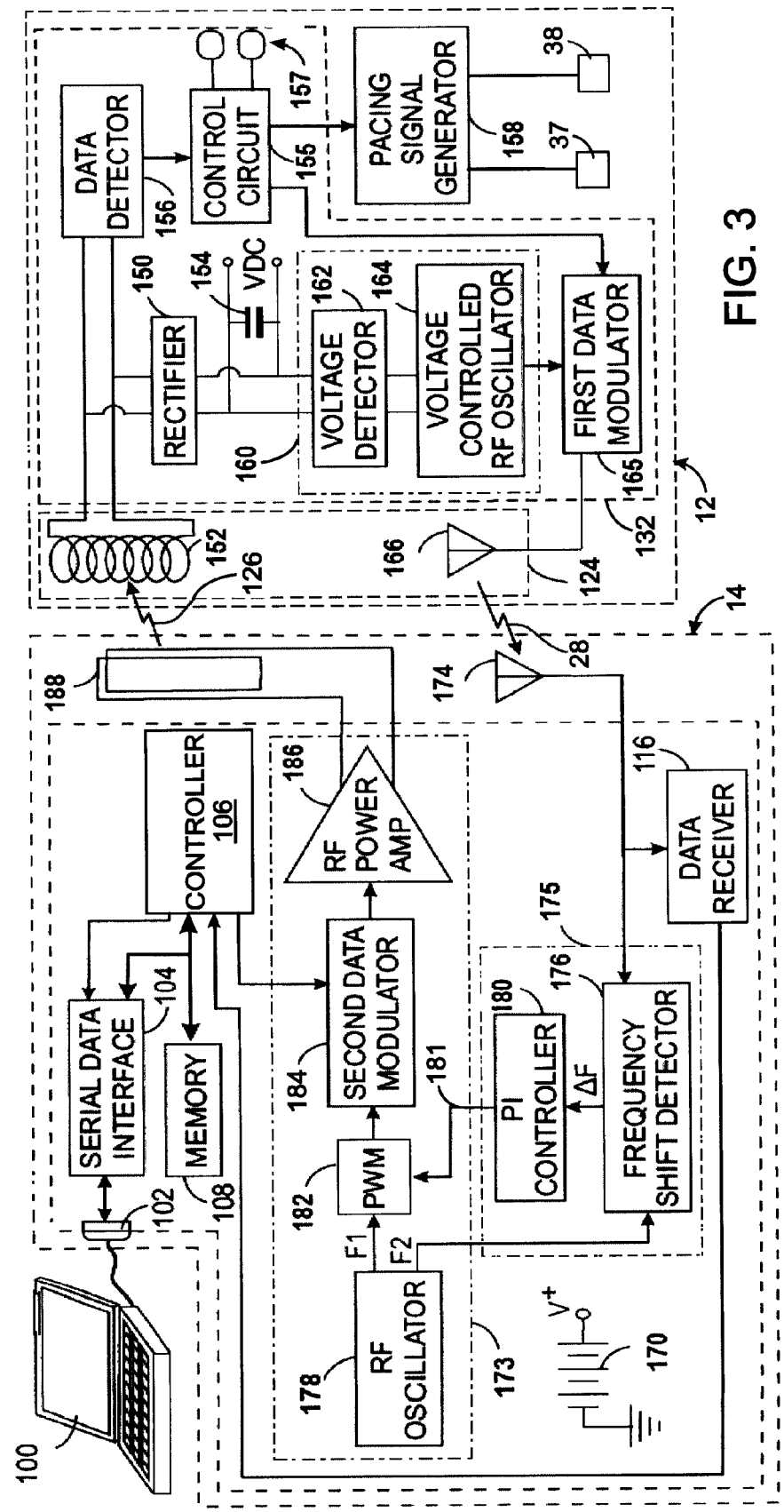
FIG. 3 is a detailed block diagram of the external and internal components.

Referring to FIG. 3, the internal components comprise an implanted stimulator 12 includes a stimulation circuit 132 having a first receive antenna 152 within the antenna assembly 124 in which the antenna is tuned to pick-up a first RF signal 26 at a first radio frequency. The first receive antenna 152 is coupled to a data detector 156 that recovers data and commands carried by the first RF signal 26. That data specifies operational parameters for the stimulator 12, such as the duration that a stimulation pulse is applied to the electrodes 37 and 38. The recovered data is sent to a control circuit 155 for that stimulator, which stores the operational parameters for use in controlling operation of a pacing signal generator 158 that applies tissue stimulating voltage pulses across the electrodes 37 and 38.

The control circuit 155 also is connected to a pair of sensor electrodes 157 that detect electrical activity of the heart and provide conventional electrocardiogram signals which are utilized to determine when cardiac pacing should occur. Additional sensors for other physiological characteristics, such as temperature, blood pressure or blood flow, may be provided and connected to the control circuit 155. The control circuit stores a histogram of pacing, data related to usage of the stimulator, and other information which can be communicated to the extracorporeal power source 14 or another form of a data gathering device that is external to the patient.

The first receive antenna 152 also is connected to a rectifier 150 that extracts energy from the received first RF signal. That energy is used to charge a storage capacitor 154 that supplies electrical power to the components of the implanted stimulator 12. Specifically, the radio frequency, first RF signal 26 is rectified to produce a DC voltage (VDC) that is applied across the storage capacitor 154.

The DC voltage produced by the rectifier 150 also is applied to a feedback signal generator 160 comprising a voltage detector 162 and a voltage controlled, first radio frequency oscillator 164. The voltage detector 162 senses and compares the DC voltage to a nominal voltage level desired for powering the stimulator 12. The result of that comparison is a control voltage that indicates the relationship of the actual DC voltage derived from the received first RF signal 26 and the nominal voltage level. The control voltage is fed to the control input of the voltage controlled, first radio frequency oscillator 164 which produces an output signal at a radio frequency that varies as a function of the control voltage. That output signal is applied to via a first data modulator 165 to a first transmit antenna 166 of the implanted stimulator 12, which thereby emits a second RF signal 28. Data regarding physiological conditions of the animal and the status of the stimulator 15 are sent from the control circuit 155 to the first data modulator 165 which amplitude modulates the second RF signal 28 with that data.

As noted previously, the electrical energy for powering the stimulator 12 is derived from the first RF signal sent by the extracorporeal power source 14. The extracorporeal power source 14 uses power from a rechargeable battery 170 to periodically transmit pulses of the first RF signal 26. The first RF signal 26 is pulse width modulated to vary the magnitude of energy received by the implanted stimulator 12. The pulse width modulation is manipulated to control the amount of energy the stimulator receives to ensure that it is sufficiently powered without wasting energy from the battery 170 in the extracorporeal power source 14. Alternatively, the first RF signal 26 can also be modulated by amplitude modulation to vary the magnitude of energy received by the implanted stimulator 12.

To control the energy of the first RF signal 26, the extracorporeal power source 14 contains a second receive antenna 174 that picks up the second RF signal 28 from the implanted stimulator 12. Amplitude modulated data is extracted from the second RF signal 28 by a data receiver 116 and sent to the controller 106. Because the second RF signal 28 also indicates the level of energy received by stimulator 12, this enables extracorporeal power source 14 to determine whether stimulator should receive more or less energy. The second RF signal 28 is sent from the second receive antenna 174 to a feedback controller 175 which comprises a frequency shift detector 176 and a proportional-integral (PI) controller 180. The second RF signal 28 is applied to the frequency shift detector 176 which also receives a reference signal at the second frequency from a second radio frequency oscillator 178. The frequency shift detector 176 compares the frequency of the received second RF signal 28 to the second frequency and produces a deviation signal ΔF indicating a direction and an amount, if any, that the frequency of the second RF signal has been shifted from the second frequency. As described previously, the voltage controlled, first radio frequency oscillator 164, in the stimulator 12, shifts the frequency of the second RF signal 28 by an amount that indicates the voltage from rectifier 150 and thus the level of energy derived from the first RF signal 26 for powering the implanted stimulator 12.

The deviation signal ΔF is applied to the input of the proportional-integral controller 180 that produces an error on line 181 indicating the amount that the voltage (VDC) derived by the implanted stimulator 12 from the first RF signal 26 deviates from the nominal voltage level. That error signal corresponds to an arithmetic difference between a setpoint frequency and the product of a time independent constant gain factor, and the time integral of the deviation signal.

The error signal is sent to the control input of a pulse width modulator (PWM) 182 which forms an amplitude modulator within a power transmitter 173 and produces at output signal that is on-off modulated as directed by the error input. The output from the pulse width modulator 182 is fed to a second data modulator 184 which modulates the signal with data from the controller 106 for the stimulator 15. The second data modulator 184 feeds the RF signal to a power amplifier 186 from which the signal is applied to a second transmit antenna 188.

In addition to transmitting electrical energy to the implanted stimulator 15, the extracorporeal power source 14 transmits operational parameters which configure the functionality of the stimulator. The implanted stimulator 15 also sends operational data to the extracorporeal power supply. A data input device, such as a personal computer 100, enables a physician or other medical personnel to specify operating parameters for the implanted stimulator 15. Such operating parameters may define the duration of each stimulation pulse, an interval between atrial and ventricular pacing, and thresholds for initiating pacing. The data defining those operating parameters are transferred to the extracorporeal power source 14 via a connector 102 connected to the input of a serial data interface 104. The data received by the serial data interface 104 can be applied to a microprocessor based controller 106 or stored directly in a memory 108.

Figure 4:
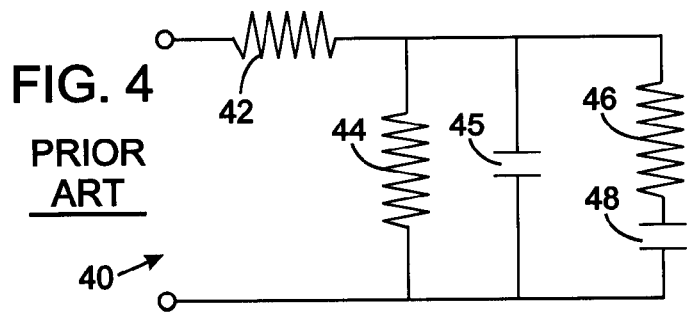
FIG. 4 is an equivalent circuit diagram of a high impedance lead used previously in cardiac pacemakers.

With reference to FIG. 4 a conventional pacing lead circuit 40 is typically characterized by a high series resistance 42 in the range of 200 ohms to 1.5 kilohms, with a nominal value of 600 ohms. This high resistance is an intentional design characteristic to limit the current from a capacitance 45, which typically is approximately 7 μF. In order to represent the tissue resistance at DC, a resistance 44 is added in parallel to the capacitance 45. The electrical characteristics of the tissue being stimulated are modeled as an equivalent resistance 46 in series with an equivalent capacitance 48 that are in parallel with the capacitance 45. The equivalent resistance is derived from a concatenated lattice comprising a series resistance and a capacitor connected to the lead commons.

Figure 5:
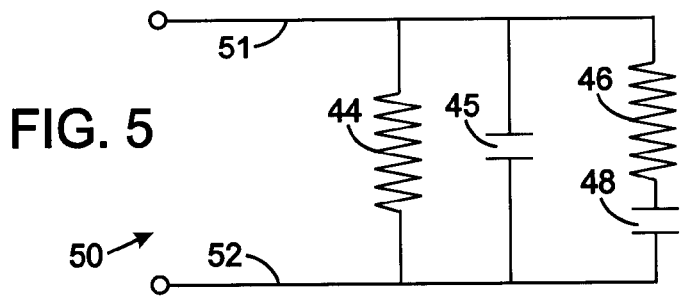
FIG. 5 is an equivalent circuit diagram of electrical conductors used with the internal component of the transvascular platform.

FIG. 5 a novel ultra low resistance pacing lead circuit 50 used in the present stimulation system as denoted by the absence of a series resistance, such as resistance 42 in FIG. 3. The pacing lead circuit 50 has first and second conductors 51 and 52, the combined resistance of which less than 100 ohms, and preferably is less than ten ohms. The electrical characteristics of the tissue being stimulated are modeled as an equivalent resistance 56 in series with an equivalent capacitance 58 that are in parallel with the capacitance 55 and resistance 54. As a result, the pacing lead circuit 50 has a significantly smaller RC time constant, which consequently speeds up the rise time of the stimulation pulse.

Upon activation of the transvascular platform 10 shown in FIG. 3, the control circuit 155 begins executing software that determines when and how to stimulate the animal's tissue. The control circuit 155 receives signals form the from the sensor electrodes 157 that indicate the electrical activity of the heart and analyzes those signals to detect irregular or abnormal cardiac activity. In response to detecting such activity, a command is sent to the pacing signal generator 158 which causes that latter device to apply an electrical voltage pulse across the stimulation electrodes 37 and 38.

Figure 6:
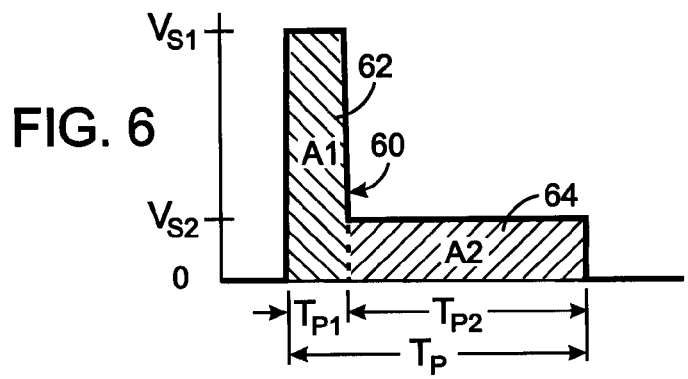
FIG. 6 depicts one period of a composite stimulation pulse according to the present invention.

The waveform of that electrical voltage pulse, referred to as a composite pacing pulse, is illustrated in FIG. 6. The composite pacing pulse 60 is characterized by a first segment 62 and a second segment 64 contiguous with the first segment, and preferably immediately following the first segment as illustrated. Both of the first and second segments 62 and 64 have rectangular shapes with the understanding that in actuality a rectangular pulse has leading edge that does not have an infinite slope and thus has a non-zero rise time. Similarly the trailing edge of the first segment also has a non-zero fall time. Specifically, the first segment 62 has a fast rise time (4V/10 μs); a duration between 0.005 ms and 0.5 ms, preferably 0.4 ms; and a similarly fast fall time.

The amplitude $V_{S1}$ of the first segment 62 is at least three times greater than the amplitude $V_{S2}$ of the second segment 64. The second segment 64 has a significantly longer duration $T_{P2}$, e.g. at least three times the duration $T_{P1}$ of the first segment 62. The integral of the first segment 62 is graphical depicted by area A1 under that segment of the pulse, and integral of the second segment 64 is depicted by its area A2. Preferably, the integral of the first segment 62 is substantially equal to the integral of the second segment 64.

Figure 1:
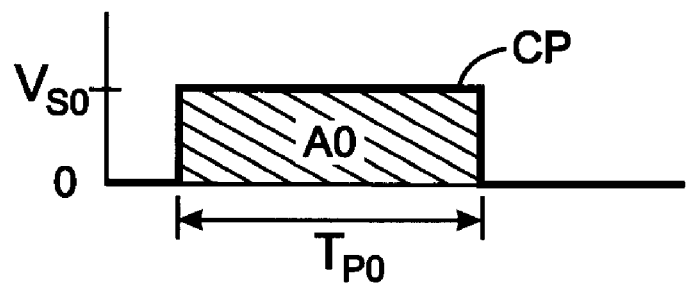
FIG. 1 is illustrates a standard stimulation pulse produced by prior cardiac pacemakers.

In comparison to the conventional pacing pulse CP shown in FIG. 1, the amplitude of the first segment 62 of the composite pacing pulse 60 is at least three times greater than the conventional nominal amplitude $V_{S0}$, while the second segment 64 has an amplitude that is less than that nominal amplitude. The total duration $T_{P0}$ of the composite pacing pulse 60 is less than the nominal duration of the conventional pacing pulse. The sum of the integrals for the first and second segments is less than the integral of the conventional pacing pulse CP in FIG. 1, i.e. total area A1+A2 of the composite pacing pulse is less than area A0. Further note that the efficiency is gained by expending less overall energy and the clinical efficacy is gained by reducing the stimulation threshold for most of the duration of the pulse.

Figure 7:
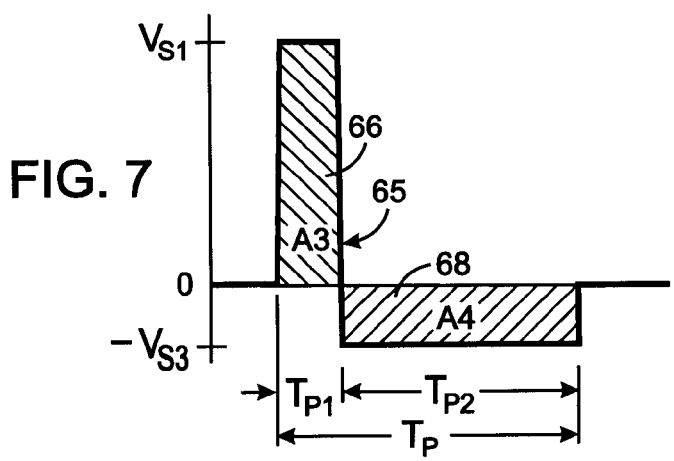
FIG. 7 depicts one period of an alternative composite stimulation pulse.

FIG. 7 illustrates an alternative composite pacing pulse 65 which is characterized by a fast rising, short duration, high positive amplitude first segment 66 that is substantially identical to the first segment 52 of the previously described pulse in FIG. 6. However, the first segment 66 is followed by a different second segment 68 consisting of a negative voltage with an absolute amplitude that is equal to or less than one-third the absolute amplitude of the first segment 66. The duration $T_{P2}$ of the second segment 64 is a significantly longer than, e.g. at least three times, the duration $T_{P1}$ of the first segment 62. Here too, the integral of the first segment 66 is substantially equal to the integral of the second segment 68.

Consequently, the sum of those integrals is less than the integral of the conventional pacing pulse CP, i.e. total area under the first and second segments A3+A4 is less than area A0 in FIG. 1.

It should be note that in contemplated embodiments, waveforms chosen may be triphasic in nature. In some embodiments, waveforms may have zero voltage between segments. In some embodiments, the stimulated tissue may be cardiac muscle, or a nerve such as vagal nerve or a spinal nerve, bladder, brain, to name only a few. As mentioned earlier, in some embodiments, traditional devices such as pacemakers and defibrillators, pacemakers for vagal stimulation for atrial fibrillation therapy, and other types of pacers for bradycardia, resynchronization, vagal stimulation for central nervous system (CNS) conditions may be benefited by the invention.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, the present invention was described in the context of a device for cardiac stimulation, but can be employed with other types of implanted stimulator systems. Accordingly, the scope of the invention should be determined from the following claims and not limited by the above disclosure.

What is claimed is:

1. A medical apparatus for artificially stimulating internal soft tissue of an animal, said apparatus comprising:
   a first electrode and a second electrode for implantation into the soft tissue inside the animal; and
   a stimulator connected to the first electrode and a second electrode, and in response to a control signal applying a composite voltage pulse to the first electrode and the second electrode for producing contraction of an organ of the animal, the composite voltage pulse having a first segment and a second segment contiguous with the first segment, an amplitude of the first segment being at least three times greater than an amplitude of the second segment, and wherein the first segment precedes the second segment.

2. The medical apparatus as recited in claim 1 wherein the first segment and the second segment of the composite voltage each have rectangular pulse shapes.

3. The medical apparatus as recited in claim 1 wherein the first segment of the composite voltage has a rise time that is at least 4 volts per 10 microseconds.

4. The medical apparatus as recited in claim 1 wherein the composite voltage pulse has a duration less than 0.5 milliseconds.

5. The medical apparatus as recited in claim 1 wherein the composite voltage pulse has a duration between 0.005 and 0.5 milliseconds.

6. The medical apparatus as recited in claim 1 wherein the second segment has a duration that is at least three times a duration of the first segment.

7. The medical apparatus as recited in claim 1 wherein an integral of the first segment is substantially equal to an integral of the second segment.

8. The medical apparatus as recited in claim 1 wherein both the first segment and the second segment are positive with respect to a reference voltage level.

9. The medical apparatus as recited in claim 1 wherein the first segment is positive with respect to a reference voltage level, and the second segment is negative with respect to the reference voltage level.

10. The medical apparatus as recited in claim 1 further comprising a first conductor connecting the first electrode to the stimulator; and a second conductor connecting the second electrode to the stimulator, wherein the first and second conductors have a combined a resistance that is less than 100 ohms.

11. The medical apparatus as recited in claim 1 further comprising a first conductor connecting the first electrode to the stimulator; and a second conductor connecting the second electrode to the stimulator, wherein the first and second conductors have a combined a resistance that is less than ten ohms.

12. The medical apparatus as recited in claim 1 wherein the stimulator is adapted for implantation into the animal.

13. The medical apparatus as recited in claim 1 wherein the stimulator further comprises a receiver for a wireless signal and a circuit for extracting electrical energy from the wireless signal for powering the stimulator.

14. A method for artificially stimulating internal soft tissue of an animal, comprising in response to a control signal applying a composite voltage pulse to a first electrode and a second electrode that are implanted into the soft tissue, the composite voltage pulse having a first segment and a second segment contiguous with and subsequent in time to the first segment, amplitude of the first segment being at least three times greater than the amplitude of the second segment, wherein the composite voltage pulse produces contraction of an organ of the animal.

15. The method as recited in claim 14 wherein the first segment and the second segment of the composite voltage pulse each have rectangular pulse shapes.

16. The method as recited in claim 14 wherein the first segment of the composite voltage has a rise time that is at least 4 volts per 10 microseconds.

17. The method as recited in claim 14 wherein the composite voltage pulse has a duration less than 0.5 milliseconds.

18. The method as recited in claim 14 wherein the composite voltage pulse has a duration between 0.005 and 0.5 milliseconds.

19. The method as recited in claim 14 wherein the second segment has a duration that is at least three times a duration of the first segment.

20. The method as recited in claim 14 wherein an integral of the first segment is substantially equal to an integral of the second segment.

21. The method as recited in claim 14 wherein both the first segment and the second segment are positive with respect to a reference voltage level.

22. The method as recited in claim 14 wherein the first segment is positive with respect to a reference voltage level, and the second segment is negative with respect to the reference voltage level.

23. The method as recited in claim 14 further comprising:
   receiving a wireless signal;
   extracting electrical energy from the wireless signal; and
   using the electrical energy to produce the composite voltage pulse.

24. A medical apparatus for artificially stimulating internal soft tissue of an animal, said apparatus comprising:
   a first electrode and a second electrode for implantation into the internal soft tissue inside the animal;
   a stimulator connected to the first electrode and a second electrode, and in response to a control signal applying a composite voltage pulse to the first electrode and the second electrode, the composite voltage pulse having a first segment and a second segment contiguous with the first segment, wherein the first segment precedes the second segment, and wherein an amplitude of the first segment being at least three times greater than an amplitude of the second segment;

a first conductor connecting the first electrode to the stimulator; and a second conductor connecting the second electrode to the stimulator, wherein the first and second conductors have a combined a resistance that is less than ten ohms.

* * * * *